United States Patent [19]  [11] 3,985,679
Taylor et al.  [45] Oct. 12, 1976

[54] TRANSITION METAL CATALYST SUPPORTED ON PARTICULATE HIGH SURFACE AREA BBB TYPE POLYMER

[75] Inventors: Paul D. Taylor, Clinton; Anthony B. Conciatori, Chatham; Rufus S. Jones, Jr., Randolph, all of N.J.

[73] Assignee: Celanese Corporation, New York, N.Y.

[22] Filed: Apr. 28, 1975

[21] Appl. No.: 572,047

[52] U.S. Cl. .............................................. 252/430
[51] Int. Cl.$^2$ ..................... B01J 31/06; B01J 31/28
[58] Field of Search ................................... 252/430

[56] References Cited
UNITED STATES PATENTS

| | | | |
|---|---|---|---|
| 3,493,343 | 2/1970 | Logan et al. | 252/430 |
| 3,574,171 | 4/1971 | Chenevey et al. | 260/78.4 R |
| 3,578,609 | 5/1971 | Haag et al. | 252/430 |
| 3,636,159 | 1/1972 | Solomon et al. | 252/430 X |
| 3,652,676 | 3/1972 | Kahle et al. | 252/430 X |

*Primary Examiner*—Winston A. Douglas
*Assistant Examiner*—William G. Wright

[57] ABSTRACT

A highly dispersed supported transition metal catalyst is provided having an ability to withstand highly elevated temperatures and caustic solutions. The transition metal is distributed over the surface of a particulate BBB type polymer of unusually high surface area. The supported catalyst may be formed through the formation of a coordination complex between a transition metal salt and benzimidazonitrogen groups present upon the surface of BBB type polymer, and the subsequent reduction of the metal cations of the salt to the metallic form. The resulting supported catalyst may be utilized in a reaction zone provided at a temperature up to about 500°C., and particularly is suited for use in hydrogenation reactions, isomerization reactions, and oxidation reactions or in a fuel cell application wherein oxygen and hydrogen react to generate electrical current.

13 Claims, No Drawings

TRANSITION METAL CATALYST SUPPORTED ON PARTICULATE HIGH SURFACE AREA BBB TYPE POLYMER

BACKGROUND OF THE INVENTION

Polymer supported catalysts have been the subject of considerable investigative research. For instance, it is recognized in the art that common normally homogeneous catalysts, e.g. the metal carbonyls of cobalt, rhodium, ruthenium, platinum and palladium may be bound via a coordination complex upon various polymer supports, and utilized in that form. See, for instance, U.S. Pat. Nos. 3,636,159 and 3,652,676. It has been found, however, that the catalyst supports suggested for use in the prior art commonly are incapable of functioning at highly elevated temperatures or in more severe environments such as caustic solutions without impairment of their physical properties. Accordingly, there has remained a need for polymer supported catalysts which are capable of functioning on a satisfactory basis even under such severe operating conditions.

Also, when metal catalysts have been applied to inorganic supports, e.g. $SiO_2$, $Al_2O_3$, $ZrO_2$, $MgO$, etc., which are capable of withstanding highly elevated temperatures, difficulties have been encountered when one has attempted to achieve a uniform non-agglomerated spaced distribution of metal catalyst sites upon the support. Such difficulties commonly lead to wasted catalyst within clusters and agglomerates of metallic catalyst and to reduced catalytic activity resulting from the overabundance of catalyst. Also, the support may dissolve under basic conditions. For example, a one percent KOH solution in contact with silica gel will reduce its surface area from about 500 square meters per gram to about 300 square meters per gram in a few hours.

It is an object of the present invention to provide an improved supported transition metal catalyst.

It is an object of the present invention to provide an improved supported transition metal catalyst which is capable of utilization at highly elevated temperatures and/or in the presence of a caustic medium.

It is an object of the present invention to provide an improved supported transition metal catalyst wherein the metal uniformly is distributed at isolated sites over the surface of a high surface area particle of BBB type polymer.

It is an object of the present invention to provide a supported transition metal catalyst which particularly is suited for use in hydrogenation reactions, isomerization reactions, and oxidation reactions.

It is an object of the present invention to provide a supported transition metal catalyst which particularly is suited for use in a fuel cell wherein oxygen and hydrogen react to produce electrical current and to form water.

It is another object of the present invention to provide a process for the formation of an improved supported transition metal catalyst.

These and other objects, as well as the scope, nature, and utilization of the invention will be apparent to those skilled in the art from the following description and appended claims.

SUMMARY OF THE INVENTION

It has been found that an improved supported catalyst comprises a support of particulate BBB type polymer having a surface area of about 100 to 500 square meters per gram, and a transition metal distributed upon the surface thereof in a concentration of about 0.01 to 5 percent by weight based upon the weight of the support.

It has been found that a process for the formation of an improved supported transition metal catalyst comprises:

a. contacting particulate BBB type polymer having a surface area of about 100 to 500 square meters per gram with a solution of a salt of a transition metal wherein the benzimidazo-nitrogen groups present upon the surface of BBB type polymer form a coordination complex with the salt, b. recovering the particulate BBB type polymer bearing the coordination complex upon the surface thereof, and c. reducing the transition metal cations of the coordination complex present upon the surface of the BBB type polymer to the metallic form.

DESCRIPTION OF PREFERRED EMBODIMENTS

The catalyst support which is utilized in the present invention comprises BBB type polymer, i.e. poly(bisbenzimidazobenzophenanthroline) and related nitrogenous polymers. It is essential that the BBB type polymer possess a high surface area of about 100 to 500 square meters per gram, and preferably a surface area of about 200 to 350 square meters per gram. Such support conveniently may be formed in accordance with the teachings of commonly assigned U.S. Pat. Ser. No. 424,996, filed Dec. 14, 1973, and entitled "Production of Particulate BBB Type Polymer Having an Unusually High Surface Area."

As is known in the art these polymers are made by condensing at least one organic tetra-amine with at least one tetracarboxylic acid (which also may be in the form of the corresponding half anhydride or dianhydride).

The Organic Tetra-Amine

The organic tetra-amine has a structural formula

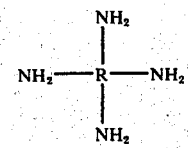

wherein R is an aromatic or cycloaliphatic tetravalent radical and wherein each of the four amino groups is attached directly to a carbon atom present in a ring of said aromatic or cycloaliphatic radical in a position which is ortho or peri to another carbon atom to which another of said amino groups is also directly attached. When R is an amino substituted naphthalene, the carbon atoms at the 1 and 8 positions are considered to be peri to each other as are the carbon atoms at the 4 and 5 positions. Five or six member rings are formed depending upon whether R is ortho or peri amino substituted respectively, as will be apparent to those skilled in the art. It is preferred that R be an aromatic radical rather than a cycloaliphatic radical. It is preferred that R contain up to about 20 carbon atoms.

Non-limiting examples of the tetra-amine monomers which may be used individually or in mutual admixture in forming the desired polymers are: 3, 3′-diaminobenzidine; bis(3,4-diamino phenyl) methane; 1,2-bis(3,4-diamino phenyl) ethane; 2,2-bis(3,4-diamino phenyl) propane; bis (3,4-diamino phenyl) ether; bis (3,4-diamino phenyl) sulfide; bis (3,4-diamino phenyl) sulfone; 1,2,4,5-tetraamino benzene; 1,4,5,8-tetra-aminonaphthalene; 2,3,6,7-tetraaminonaphthalene; etc.; and the corresponding ring-hydrogenated tetra-amines.

The Tetracarboxylic Acid

The tetracarboxylic acid (which also may be in the form of the corresponding half anhydride or dianhydride) has the structural formula

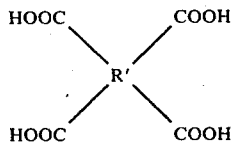

wherein R′ is a tetravalent aromatic or cycloaliphatic radical wherein each of the four carboxyl groups is attached directly to a carbon atom present in a ring of said aromatic or cycloaliphatic radical in a position which is ortho or peri to another carbon atom to which another of said carboxyl groups is also directly attached. When R′ is a carboxyl substituted bicyclic fused ring compound, such as tetra-carboxyl substituted naphthalene, the carbon atoms at the 1 and 8 positions are considered to be peri to each other, as are the carbon atoms at the 4 and 5 positions. Five or six member rings are formed depending upon whether R′ is ortho or peri carboxyl substituted respectively, as will be apparent to those skilled in the art. It is preferred that R′ be an aromatic radical rather than a cycloaliphatic radical. It is preferred that R′ contain up to about 20 carbon atoms.

Non-limiting examples of the tetracarboxylic acids include: pyromellitic acid, i.e. 1,2,4,5-benzenetetracarboxylic acid; 2,3,6,7-naphthalene tetracarboxylic acid; 3,3′,4,4′-diphenyl tetracarboxylic acid; 1,4,5,8-naphthalene tetracarboxylic acid; 2,2′,3,3′-diphenyl tetracarboxylic acid; 2,2-bis(3,4-dicarboxyphenyl) propane; bis(3,4-dicarboxylphenyl) sulfone; 3,4,9,10-perylene tetracarboxylic acid; bis(3,4-dicarboxyphenyl)ethers; ethylene tetracarboxylic acid, naphthalene-1,2,4,5-tetracarboxylic acid; decahydronaphthalene-1,4,5,8-tetracarboxylic acid; 4,8-dimethyl-1,2,3,5,6-hexahydronaphthalene-1,2,5,6-tetracarboxylic acid; 2,6-dichloronaphthalene-1,4,5,8-tetracarboxylic acid; 2,7-dichloronaphthalene-1,4,5,8-tetracarboxylic acid; 2,3,6,7-tetrachloronaphthalene-1,4 5,8-tetracarboxylic acid; phenanthrene-1,8,9,10-tetracarboxylic acid; cyclopentane-1,2,3,4-tetracarboxylic acid; pyrrolidine-2,3,4,5-tetracarboxylic acid; pyrazine-2,3,5,6-tetracarboxylic acid; 2,2-bis(2,3-dicarboxyphenyl) propane; 1,1-bis(2,3-dicarboxyphenyl) ethane; 1,1-bis(3,4-dicarboxyphenyl) ethane; bis(2,3-dicarboxyphenyl) methane; bis(3,4-dicarboxyphenyl) methane; benzene-1,2,3,4-tetracarboxylic acid; 1,2,3,4-butane tetracarboxylic acid; thiophene-2,3,4,5-tetracarboxylic acid; and similar acids, as well as the half anhydrides (i.e. mono anhydrides) or dianhydrides of such acids. The preferred tetracarboxylic acids contain carboxyl groups peri substituted upon a naphthalene nucleus.

Formation of the BBB Type Polymer Support

In accordance with the teachings of U.S. Pat. Ser. No. 424,996, the polymerization medium may comprise a major concentration of a liquid sulfone which is inert under the reaction conditions. The sulfone polymerization medium may possess the structural formula R—SO$_2$—R′ wherein R and R′ are the same or different aryl, alkyl, or alkoxy group (e.g. —OR″ where R″ is an alkyl group). Preferably, at least one of the R or R″ groups is an aryl group. Alternatively, the sulfone polymerization medium may be cyclic in nature wherein R and R′ are linked to form a common ring structure (e.g. O$_2$S⊂R). Also, more than one sulfone group may be present in a given molecule of the polymerization medium. It is essential that the sulfone polymerization medium be free of any substituent groups which would undergo reaction with the condensation reactants or the BBB type polymer product, e.g. amino groups, carboxyl groups, or halogen groups.

The sulfone utilized possesses a relatively high boiling point, and commonly is a solid at ambient conditions. Under the condensation reaction conditions selected the sulfone is a liquid. The sulfone preferably possesses a boiling point in excess of 300° C. (e.g. a boiling point of about 300 to 450° C.), and most preferably a boiling point of about 325 to 420° C. It is preferable that the sulfone polymerization medium inherently be a liquid at the condensation reaction temperature selected (described hereafter) and at substantially atmospheric pressure, otherwise superatmospheric condensation reaction conditions must be utilized.

Representative sulfone polymerization media suitable for use in the present process are as follows: diphenyl sulfone (boiling point about 378° to 379° C.); 4,4′-ditolyl sulfone (boiling point 405° C. at 714 mm. Hg); methylphenyl sulfone; ethylphenyl sulfone; 4,4′-diethoxy sulfone; 1,2-bis(phenylsulfonyl) ethane, etc. The preferred sulfone polymerization media are diphenyl sulfone; 4,4′-ditolyl sulfone; and methylphenyl sulfone.

The particularly preferred sulfone polymerization medium is diphenyl sulfone. In this compound both R and R′ are simple phenyl groups. Diphenyl sulfone is an example of a high boiling sulfone which is a solid at room temperature and a liquid at the condensation reaction temperature, and is sometimes identified as phenyl sulfone or sulfobenzide. The melting point of diphenyl sulfone is about 128° to 129° C.

A low boiling organic solvent for the condensation reactants and the sulfone optionally may be initially provided in admixture therewith prior to raising the temperature of the condensation reactants to reaction temperature (described hereafter) with the low boiling organic solvent being substantially volatilized prior to the reactants reaching reaction temperature. The low boiling organic solvent does not undergo any substantial chemical reaction while present in the condensation reaction zone and can be considered inert with respect to the condensation reactants. The low boiling organic solvent possesses a boiling point below about 200° C., e.g. a boiling point of about 80° to 200° C. The boiling point of the low boiling organic solvent should be above the melting point of the sulfone polymerization medium but sufficiently low to allow for its volatilization prior to reaching polymerization temperature. The low boiling organic solvent serves the role of aiding in the formation of a homogeneous reaction mixture in the shortest possible time. In the absence of the low boiling organic solvent the sulfone polymerization medium must be heated until molten before a homogeneous admixture can be formed.

Representative low boiling organic solvents which optionally may be utilized include: para-xylene, toluene, ortho-xylene, metaxylene, methylethyl benzenes, cumene (i.e. isopropyl benzene), cymene, chlorobenzene, anisole, ethoxy benzene, decahydronaphthalene (cis- and trans-), decane, nonane, tetrahydronaphthalene, etc.

Preferred low boiling organic solvents are para-xylene, chlorobenzene, and cumene. The particularly preferred low boiling organic solvent is para-xylene.

The condensation reaction wherein the particulate BBB type polymer is formed may be conducted while the condensation reactants are agitated in the presence of a major concentration of the liquid sulfone polymerization medium (heretofore described) at a temperature of about 300° to 450° C., e.g. at about 325° to 420° C. The preferred reaction temperature when employing a diphenyl sulfone polymerization medium is about 350° to 380° C. The tetra-amine and the tetracarboxylic acid or its corresponding half anhydride or dianhydride preferably are provided in substantially stoichiometric concentrations. The condensation reactants commonly are provided in a total concentration of about 5 to 25 percent by weight based upon the total weight of the condensation reactants and the sulfone polymerization medium, e.g. in a concentration of about 10 to 20 percent by weight. In a preferred embodiment the condensation reaction is carried out at substantially atmospheric pressure. However, superatmospheric pressures up to about 200 psig alternatively may be employed. It is, of course, understood that the boiling point of the sulfone polymerization medium must not be exceeded during the condensation reaction and accordingly may influence the exact temperature selected for the condensation reaction.

When no low boiling organic solvent is utilized, the condensation reactants and the sulfone polymerization medium may be brought to reaction temperature by slowly heating an intimate admixture of the same until the melting point of the sulfone is reached. The reaction should be stirred continuously to insure even heating.

In the embodiment of the process wherein a low boiling organic solvent is utilized, it commonly is provided in a concentration of about 20 to 70 percent by weight based upon the total weight of the condensation reactants, e.g. in a concentration of about 35 to 65 percent by weight.

When utilizing the low boiling organic solvent in the process, the tetra-amine condensation reactant and the sulfone polymerization medium tend initially to dissolve in the same at room temperature. As the mixture is heated the tetracarboxylic acid or corresponding half anhydride or dianhydride is dissolved. The contents of the reaction zone may be brought to the desired reaction temperature by external heating at moderately rapid rate, e.g. at about 5° to 15° C./minute. As the boiling point of the low boiling organic solvent is exceeded, it is allowed to volatilize and to be removed from the reaction zone.

The condensation reaction preferably is conducted in the absence of air so that the organic tetra-amine will not be appreciably oxidized by oxygen in a competing reaction.

It is preferred that the molecular weight of the polymer formed be such that its inherent viscosity is at least 0.2dl./gram (e.g. 0.2 to 3.0 dl./grams), and most preferably 0.4 to 2.5 dl./gram. The inherent viscosity is measured at 25° C. at a concentration of 0.4 g. of polymer per 100 ml. of solvent. Ninety-seven percent sulfuric acid (by weight) is a convenient and preferred solvent for the purpose of this invention though other solvents may be used similarly. The viscosity of the polymer solution is measured relative to that of the solvent alone and the inherent viscosity (I.V.) is determined from the following equation:

$$I.V. = \frac{\ln V_2/V_1}{C}$$

In the above formula, $V_2$ is the efflux time of the solution, $V_1$ is the efflux time of the solvent, and C is the concentration expressed in grams of polymer per 100 ml. of solution. As is known in the polymer art, inherent viscosity is monotonically related to the molecular weight of the polymer.

Commonly, condensation reaction times of about 0.5 to 10 hours are adequate to complete the desired degree of polymerization e.g. about 2.5 to 5 hours. The water by-product may be volatilized as it is formed.

As the condensation reaction progresses, the BBB type polymer assumes the configuration of a particulate solid of extremely small particle size. Such particulate solid begins to appear soon after the reactants reach reaction temperature, and is suspended within the sulfone polymerization medium via agitation as the reaction proceeds. Commonly particulate BBB type polymer is formed in the present process having an unusually high surface area about 100 to 500, or more, square meters per gram, e.g. about 200 to 350 square meters per gram. The surface area of the resulting product may be determined by any technique commonly utilized in such measurement, such as nitrogen adsorption utilizing the Brunauer-Emmett-Teller adsorption isotherm.

The particulate BBB type polymer of unusually small particle size may be recovered at the completion of the condensation reaction by any convenient technique such as filtration of the mixture above the melting point of the sulfone polymerization medium, or by the addition of solvent capable of dissolving the sulfone polymerization medium and not the polymer product, followed by filtration. It is recommended that the isolated polymer be mixed with suitable solvents to remove remaining traces of the sulfone polymerization medium and/or unreacted monomer, and again isolated by filtration.

If desired, the particulate BBB type polymer optionally may be treated in certain alkaline solutions to remove unstable linkages in accordance with the teachings of commonly assigned U.S. Pat. No. 3,574,171.

The Introduction of the Transition Metal Catalyst

A coordination complex initially is formed wherein a salt of a transition metal becomes bound with the benzimidazo-nitrogen groups present upon the surface of the BBB type polymer. The coordination complex is linked via the nitrogen atom of the amide and/or imide groups (i.e. the benzimidazo-nitrogen groups). Approximately one molecule of the salt of a transition metal is complexed with each nitrogen atom on the surface of the BBB type polymer. The thus absorbed transition metal salt is bound exclusively at isolated sites over the surface of the BBB type polymer.

The coordination complex may be simply formed by contacting the high surface area BBB type polymer with a solution of a salt of the transition metal. The desired complex immediately forms upon contact. In a preferred embodiment of the invention the salt of the transition metal is provided in an aqueous solution when contacted with the high surface area BBB type polymer. For instance, a water-soluble salt of the transition metal may be present in a water solvent in a concentration of about 0.01 to 10 percent by weight based upon the total weight of the solution when contact is made. The temperature of the solution conveniently may be provided at about 5° to 95° C. The presence of the coordination complex upon the surface of the high surface area BBB type polymer may be detected by color changes in the supernatant liquid due to the lowering of the concentration of the salt dissolved therein, or other suitable analysis.

In a preferred embodiment of the process salts of Group VIIIB transition metals are utilized. For instance, representative water-soluble salts of Group VIIIB transition metals include: cobalt nitrate, nickel nitrate, ferric nitrate, rhodium chloride, palladium nitrate, sodium tetrachloropalladate, potassium tetrachloroplatinate, chloroplatinous acid, chloropalladous acid, gold nitrate, and mixed salts of the above. Water-soluble salts of other transition metals, such as copper nitrate, likewise may be selected.

The solution of the salt of a transition metal alternatively may be provided with the use of a non-aqueous solvent which does not deleteriously influence the particulate BBB type polymer.

Non-aqueous solvents such as methanol, diethylether, dioxane, pentane, benzene, etc. may be utilized. The transition metal salts which are dissolved in such non-aqueous solvents may be soluble metal complexes, metal carbonyls, and water-sensitive metal alkyls, e.g. rhodium $(CO_2)$ (cyclooctadiene)$_2$, dicobaltoctacarbonyl, nickel carbonyl, tungsten VI chloride, and transition metal Group VIII alkyls. Mixed metal compounds such as $Rh_6(CO)_{16}$, $Re_2(CO)_{10}$, likewise may be selected.

The particulate BBB type polymer bearing the coordination complex next is recovered (i.e. the support is separated from the solution). The catalyst recovery may be carried out in any convenient manner as will be apparent to those skilled in the art. For instance, the solution may be removed by filtration, decantation, centrifugation, or simple removal of the solvent by evaporation when a substantial portion of the transition metal salt present in the solution has been complexed with the BBB type polymer. In a particularly preferred embodiment of the process the solution simply is removed by filtration.

The transition metal cations of the coordination complex present upon the surface of the BBB type polymer next are reduced or thermally decomposed to metallic form. The resulting transition metal is distributed exclusively at isolated sites over the surface of the BBB type polymer which generally correspond to the location of the benzimidazo-nitrogen groups near the polymer surface. The reduction of the metal cations conveniently may be carried out by contact with hydrogen at a temperature of about 25° to 400° C. Representative alternate reduction procedures include reducing with hydrazine hydrate, carbon monoxide, ethylene, or other well known reducing agents. The presence of the transition metal upon the surface of the high surface area BBB type polymer may be detected by electron microscopy, transmission electron microscopy, induced electron emission, X-ray fluorescence, or other suitable analysis.

The resulting supported catalyst comprises a support of particulate BBB type polymer having a surface area of about 100 to 500 square meters per gram, and a transition metal distributed upon the surface thereof in a concentration of about 0.01 to 5 percent by weight based upon the weight of the support. In a particularly preferred embodiment the transition metal is distributed upon the surface of the BBB type polymer support in a concentration of about 0.1 to 4 percent by weight of the support.

In a further embodiment of the invention the support need not be composed entirely of BBB type polymer so long as the surface of the support comprises this polymer. For instance, a high surface area particle of different composition may have its surface coated with a thin layer of BBB type polymer and the resulting composite support utilized in the present invention. For instance, high surface area silica particles may be coated with a solution of BBB type polymer dissolved in sulfuric acid and the solvent removed to form a uniform coating upon the silica particles while retaining the desired high surface area. The BBB type polymer coating may comprise about 0.1 to 10 percent by weight of the total weight of the support. Other representative particles other than silica which may be coated with the BBB type polymer include: silica-alumina, zirconia, titanium oxide, alumina, thoria, glass beads or fibers, carbon, graphite, or similar materials which are not degraded by concentrated sulfuric acid at ambient conditions. The terms "particulate BBB type polymer", etc. accordingly are intended to include this embodiment of the invention so long as the surface of the support comprises BBB type polymer. The use of an inexpensive core for the support has the advantage of reducing the cost of the catalyst support.

The highly dispersed nature of the supported transition metal catalyst enables efficient catalytic activity while minimizing the overall quantity of catalyst required. The supported catalyst particularly is suited for use in environments wherein high temperature resistance (e.g. up to about 500° C.) is desirable and/or wherein caustic solutions are encountered. For instance, the supported catalyst may be used in a high temperature fuel cell electrode wherein oxygen and hydrogen react to produce electrical energy and to form water.

Alternatively, the supported catalyst may be used in a variety of hydrogenation reactions. For instance, linear or cyclic olefins containing 2 to 20 carbon atoms may be hydrogenated. Olefin isomerization and oxidation reactions also may be carried out in the presence of the supported catalyst. For instance, the reactants may be passed one or more times over the static supported catalyst.

The following examples are given as specific illustrations of the invention. It should be understood, however, that the invention is not limited to the specific details set forth in the examples. In each example particulate poly(bisbenzimidazobenzophenanthroline) polymer of unusually high surface area was formed in accordance with teachings of U.S. Pat. Ser. No. 424,996 by the condensation of 1,4,5,8-naphthalene tetracarboxylic acid and 3,3'-diamino benzidine to form a fully cyclicized polymer one isomer of which is illustrated in the following equation:

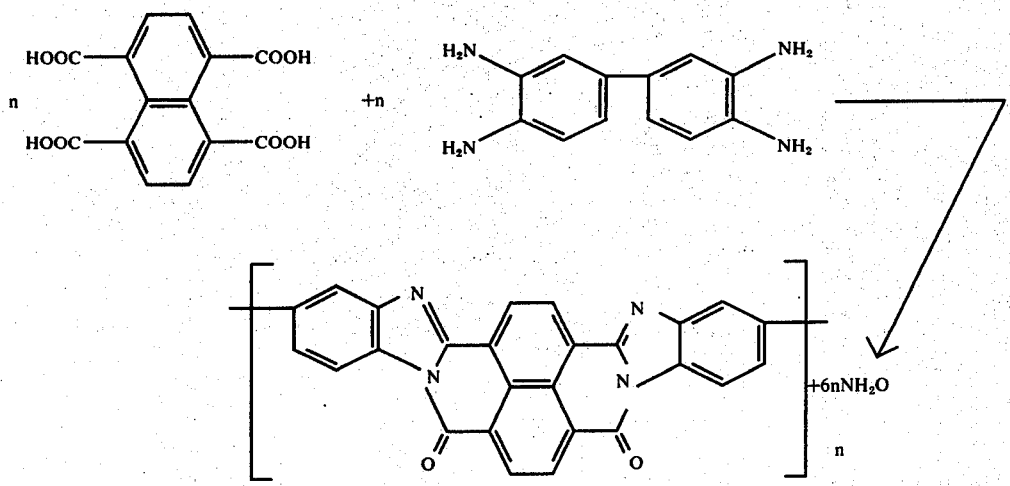

The specific isomer illustrated may be identified as poly[6,9-dihydro6,9-dioxobisbenzimidazo(2,1-b:1',2'-j)benzo(lmn) (3,8) phenanthroline-2,13-diyl]. It will be apparent to those skilled in the art that various additional isomers will also be produced during the condensation reaction. The particulate poly(bisbenzimidazobenzophenanthroline) polymer exhibits a surface area of about 290 square meters per gram as determined by BET nitrogen adsorption analysis.

EXAMPLE I 0.0316 gram of palladium dichloride [i.e. $PdCl_2$] was dissolved in 100 ml. of water by adding 0.0207 gram sodium chloride and heating to 70° C. Sodium tetrachloropalladate [i.e. $Na_2PdCl_4$] forms. 0.45 gram of the particulate BBB type polymer was added to the resulting solution and stirred at room temperature [i.e. 25° C.] for 18 hours. During this time the supernatant solution changed from a light brown color to nearly colorless as a coordination complex between the salt and the benzimidazo-nitrogen groups present upon the surface of the BBB type polymer was formed. The particulate BBB type polymer bearing the coordination complex upon its surface was separated by use of a glass fritted funnel, dried at 100° C. for 4 hours, and reduced in hydrogen at 150° C. for 4 hours. Palladium metal was distributed upon the surface of the particulate BBB type polymer in a concentration of about 4 percent by weight based upon the weight of the support.

0.1 gram of the resulting supported catalyst was placed in a recycle reactor and tested with respect to its hydrogenation activity for the conversion of propylene to propane using helium as a diluent. The recycle reactor comprised a bellows pump capable of delivering up to 6.5 liters of gas per minute at one atmosphere pressure, a one liter surge vessel, a 2 ft. × ⅛ inch glass coil gas preheater connected to a 1 inch glass frit disc filter which supported the catalyst, and connecting lines to complete a gas recycle system. Total volume of the system was 1,250 ml. Propylene, hydrogen and helium were slowly admitted to the recycle reactor at the intake of the bellows pump. An exit port carried the product to an analytical system.

The reaction conditions and results are summarized below.

| Run Number | Feed in cc./min | | | Temperature | Recycle Rate liters/min. | Mole Percent Propane at Exit |
|---|---|---|---|---|---|---|
| | Propylene | Hydrogen | Helium | | | |
| 1 | 19.3 | 10.55 | 28.2 | 144°C. | 0.1 | 20.8 |
| 2 | 19.3 | 10.55 | 30.2 | 144°C. | 1.0 | 26.0 |
| 3 | 19.3 | 10.55 | 31.6 | 144°C. | 4.0 | 29.9 |
| 4 | 19.3 | 10.55 | 31.4 | 144°C. | 6.5 | 29.3 |
| 5 | 9.8 | 10.6 | 32.3 | 101°C. | 6.5 | 14.1 |
| 6 | 10.1 | 10.6 | 33.0 | 112°C. | 6.5 | 18.3 |
| 7 | 9.6 | 11.1 | 34.0 | 131°C. | 6.5 | 24.0 |
| 8 | 7.6 | 10.6 | 37.1 | 143°C. | 6.5 | 34.9 |
| 9 | 3.7 | 10.6 | 38.5 | 142°C. | 6.5 | 39.2 |
| 10 | 10.0 | 11.1 | 35.3 | 143°C. | 6.5 | 32.2 |

EXAMPLE II

Example I is repeated with the exception that the supported catalyst is tested with respect to its hydrogenation activity for the conversion of ethylene to ethane using helium as a diluent.

The reaction conditions and result are summarized below.

| Run Number | Feed in cc./min. | | | Temperature | Recycle Rate liters/min. | Mole Percent Ethane at Exit |
|---|---|---|---|---|---|---|
| | Ethylene | Hydrogen | Helium | | | |
| 13 | 10 | 10 | 30 | 130°C. | 6.5 | 20 |

EXAMPLE III

Example I is repeated with the exception that oxygen instead of an olefin is introduced into the recycle reactor together with hydrogen and helium as a diluent to form water.

The reaction conditions and results are summarized below.

| Run Number | Oxygen | Hydrogen | Helium | Temperature | Recycle Rate liters/min | Mole Percent O$_2$ Conversion at Exit |
|---|---|---|---|---|---|---|
| 14 | 10 | 10 | 30 | 29°C. | 6.5 | 48 |

The supported catalyst of the present invention alternatively may be utilized in a fuel cell such as that illustrated on page 103 of the Advances in Chemistry Series, No. 47, "Fuel Cell Systems" (1965) by George J. Young and Henry R. Linden to generate electrical current via the reaction of oxygen and hydrogen.

EXAMPLE IV

Example I is repeated with the exception that the supported catalyst is tested with respect to its hydrogenation and isomerization activity using a 1-butene feed together with hydrogen and helium as a diluent.

The reaction conditions and result are summarized below.

| Run Number | Feed in cc./min. | | | Temperature | Recycle Rate liters/min. | Mole Percent at Exit | | |
|---|---|---|---|---|---|---|---|---|
| | 1-Butene | Hydrogen | Helium | | | Butane | cis-2- | trans-2- |
| 15 | 10 | 10 | 30 | 133°C. | 6.5 | 26 | 2.1 | 22.3 |
| 16 | 10 | 0 | 30 | 150°C. | 6.5 | 0 | 0 | 0 |

It will be noted that in the absence of hydrogen no isomerization of the 1-butene feed was observed.

Although the invention has been described with preferred embodiments, it is to be understood that variations and modifications may be resorted to as will be apparent to those skilled in the art. Such variations and modifications are to be considered within the purview and the scope of the claims appended hereto.

We claim:

1. A process for the formation of an improved supported transition metal catalyst comprising:
   a. contacting a particulate polymer possessing benzimidazo-nitrogen groups which is a condensation product of at least one organic tetra-amine with at least one tetra-carboxylic acid or the corresponding anhydride and having a surface area of about 100 to 500 square meters per gram with a solution of a salt of a transition metal wherein the benzimidazo-nitrogen groups present upon the surface of said polymer form a coordination complex with said salt,
   b. recovering said particulate polymer bearing said coordination complex upon the surface thereof, and
   c. reducing the transition metal cations of said coordination complex present upon the surface of said polymer to the metallic form.

2. A process for the formation of an improved supported transition metal catalyst in accordance with claim 1 wherein said polymer is poly(bisbenzimidazobenzophenanthroline).

3. A process for the formation of an improved supported transition metal catalyst in accordance with claim 1 wherein said particulate polymer has a surface area of about 200 to 350 square meters per gram.

4. A process for the formation of an improved supported transition metal catalyst in accordance with claim 1 wherein said transition metal is a Group VIII metal.

5. A process for the formation of an improved supported transition metal catalyst in accordance with claim 1 wherein said salt of a transition metal is water-soluble and water serves as the solvent for said solution of step (a).

6. A process for the formation of an improved supported transition metal catalyst in accordance with claim 1 wherein said reduction of said transition metal cations of said coordination complex is carried out at a temperature of about 25° to 400° C. in the presence of hydrogen.

7. A process for the formation of an improved supported transition metal catalyst comprising:
   a. contacting particulate poly(bisbenzimidazobenzophenanthroline) polymer having a surface area of about 200 to 350 square meters per gram with an aqueous solution of a water-soluble salt of a Group VIIIB metal wherein the benzimidazo-nitrogen groups present upon the surface of said polymer form a coordination complex with said salt,
   b. recovering said particulate poly(bisbenzimidazobenzophenanthroline) polymer bearing said coordination complex upon the surface thereof, and
   c. reducing the Group VIII B metal cations of said coordination complex present upon the surface of said poly(bisbenzimidazobenzophenanthroline)

polymer to the metallic form by contact with hydrogen at a temperature of about 25° to 400° C.

8. A process for the formation of an improved supported transition metal catalyst in accordance with claim 7 wherein said water-soluble salt is present in said aqueous solution of step (a) in a concentration of about 0.01 to 10 percent by weight based upon the total weight of the solution.

9. A process for the formation of an improved supported transition metal catalyst in accordance with claim 7 wherein said water-soluble salt of a Group VIII B metal is selected from the group consisting essentially of cobalt nitrate, nickel nitrate, ferric nitrate, rhodium chloride, palladium nitrate, sodium tetrachloropalladate, potassium tetrachloroplatinate, chloroplatinous acid, chloropalladous acid, gold nitrate, and mixed salts of the foregoing.

10. A supported catalyst comprising a support of particulate polymer which is a condensation product of at least one organic tetra-amine with at least one tetra-carboxylic acid or the corresponding anhydride having a surface area of about 100 to 500 square meters per gram, and a transition metal distributed upon the surface thereof in a concentration of about 0.01 to 5 percent by weight based upon the weight of said support.

11. A supported catalyst in accordance with claim 10 wherein said polymer is poly(bisbenzimidazobenzophenanthroline).

12. A supported catalyst in accordance with claim 10 wherein said transition metal is a Group VIII B metal.

13. A supported catalyst in accordance with claim 10 wherein said transition metal is distributed upon the surface thereof in a concentration of about 0.1 to 4 percent by weight based upon the weight of said support.

* * * * *